United States Patent [19]

Newton

[11] Patent Number: 4,900,302

[45] Date of Patent: Feb. 13, 1990

[54] SURGICAL IRRIGATION/ASPIRATION SET-UP KIT

[76] Inventor: Walter A. Newton, Chandler Mill Road, Ruffin, N.C. 27326

[21] Appl. No.: 674,064

[22] Filed: Nov. 19, 1984

Related U.S. Application Data

[63] Continuation-in-part of Ser. No. 568,435, Jan. 5, 1984.

[51] Int. Cl.$^4$ .............................................. A61M 1/00
[52] U.S. Cl. ........................................................ 604/30
[58] Field of Search ............................... 604/319–321, 604/118, 119, 22, 126, 151–153, 35, 30, 48, 93; 137/526; 411/191–193, 195, 196

[56] References Cited

U.S. PATENT DOCUMENTS

| | | | |
|---|---|---|---|
| 1,142,899 | 6/1915 | Lines | 411/195 |
| 3,719,197 | 3/1973 | Pannier, Jr. et al. | 137/205 |
| 4,184,510 | 1/1980 | Murry et al. | 604/30 |
| 4,258,940 | 3/1981 | Fudge | 285/307 |
| 4,346,711 | 8/1982 | Agdanowski et al. | 604/128 |
| 4,418,944 | 12/1983 | Haines et al. | 604/119 |
| 4,493,695 | 1/1985 | Cook | 604/30 |

OTHER PUBLICATIONS

ACRODISC Filters, (Avis & Akers), Sterile Preperation For The Hospital Pharmacist, 1982.

Primary Examiner—C. Fred Rosenbaum
Attorney, Agent, or Firm—C. Robert Rhodes; Judith E. Garmon

[57] ABSTRACT

A set-up kit for surgical irrigation/aspiration equipment includes an irrigation tube and a suction aspiration tube for operative connection to an irrigation/aspiration machine. The aspiration tube is releasably connected to a hexagonally-shaped nozzle means on the machined fitting, which fitting is in turn releasably connected to a receptacle containing an air passageway on the irrigation/aspiration machine. This arrangement serves to isolate the aspiration tube from the machine. To further isolate, a disposable hydrophobic filter is placed in the branch line between the machined fitting and the aspiration tube.

5 Claims, 4 Drawing Sheets

FIG. I
(PRIOR ART)

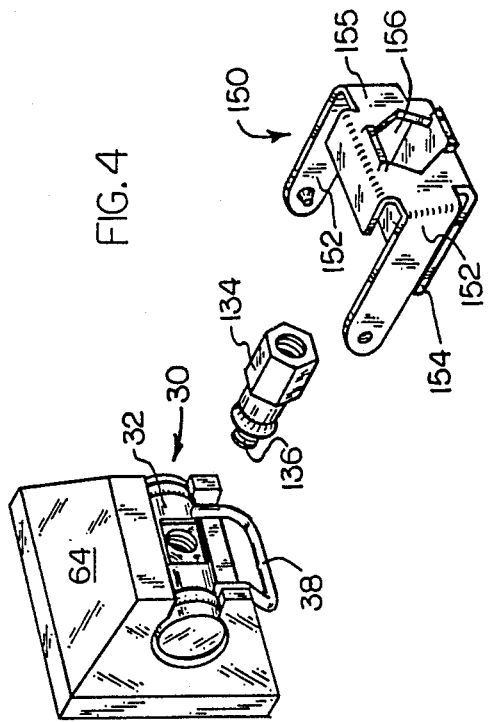
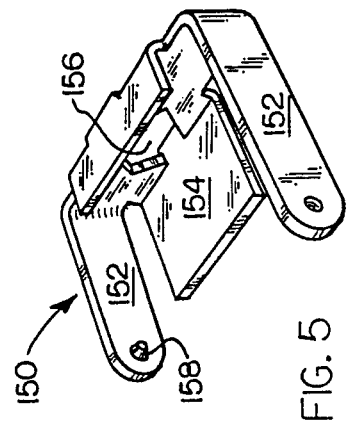

SURGICAL IRRIGATION/ASPIRATION SET-UP KIT

REFERENCE TO RELATED APPLICATIONS

This application is a continuation-in-part of an earlier application Ser. No. 568,435 filed Jan. 5, 1984.

BACKGROUND AND SUMMARY OF THE PRESENT INVENTION

During certain types of surgical procedures such as, for example, those involving the removal of cataracts from the eyes, irrigation/aspiration machines are used to provide irrigation to the operative site while removing or aspirating fluids and body tissue from the operative site. One such machine is sold under the trademark Cavitron/Kelman by Coopervision. These machines have become widely used in many types of surgery.

A disposable set-up kit consisting of irrigation and aspiration tubing is provided to the surgical team for connecting the machine to the instrument being used by the surgeon, to the sterile fluids being used for irrigation, and to the disposable collection means which receives the fluids and tissue aspirated from the site. A new set-up kit is provided with each surgical operation and is disposed of after the surgery is performed. The aforesaid set-up kit includes a disposable, plastic releasable connector called a "cam lock tee" affixed to and part of the aspiration tubing. The "cam lock tee" is snapped into place in a grooved, aspiration line receptacle on the front of the machine. This receptacle has an air orifice therein. When the connection is made, the orifice is aligned with an orifice in the "cam lock tee." So assembled there is direct communication between the aspiration line and the interior of the irrigation/aspiration machine.

Although the set-up kits are disposable and all of the instruments are sterilized prior to each surgical procedure, there are still resulting contamination problems caused by aspirant working its way into the interior of the irrigation/aspiration machines causing contamination therein, which may either interfere with proper function of the machine, or be blown back into subsequent aspiration lines. Further, aspirant in the machine may lead to the growth of bacteria and micro-organisms. In normal use air is taken into the machine and blown out. Air is taken in so that the air pressure in the line can be monitored. At other times the air outlet or air jet outlet is used to provide air into the aspiration tube at any time the suction pressure in the tube has increased to an undesirable level. This is the way the machine conventionally operates. Injection of air through the orifice breaks the suction pressure. The aforementioned growth of micro-organisms and bacteria can also cause problems at a later time when such contaminants leak into the operating room environment and possibly cause cross-contamination. Also, the injection of air through the nozzle or outlet on the same or subsequent operative cases may cause the bacteria and micro-organisms to be blown into the aspiration tube, from whence such contaminants back up to the site of the operation or contaminate the aspirant which may be subjected to later pathological tests.

In addition to contamination problems, bacause of the limited tolerance controls which can be effected on a disposible plastic "cam lock tee," the connection between the "cam lock tee" and the machine orifice is sometimes difficult to achieve properly. Sometimes the orifices do not align properly; sometimes the connection may be loose.

It was to overcoming these problems with steriliztaion of the equipment, isolation of aspirant from the equipment, and facilitating the connection of the tube that the present inventor turned his attention. The present invention is directed to an improved set-up kit in which the "cam lock tee" is replaced by a machined metallic fitting and is no longer part of the disposable aspiration line. Further, a filtering device is now inserted between the machine and the tubing. The remaining portions of the set-up kit with the irrigation/aspiration tubing and the connections for surgical instruments, I/V's and collectors, are conventional. Because of the way the connection is now made and because of the hydrophobic filter, there is a significant decrease in the growth and spreading of micro-organisms and bacteria. For the first time, the patient is isolated from the irrigation/aspiration machine and a sterile environment is maintained; aspirant is kept out of the machine; and the connection of an aspiration tube may be made more quickly, more easily, and more reliably.

In a first approach, the machined fitting includes a body portion which attaches to the grooved aspiration line receptacle by simply snap locking thereon in a manner similar to the disposable "cam lock tee." A nozzle portion of the fitting is a cylindrical tube which screws onto a nipple on the body portion. The disposable tube includes a filter device that has a male portion extending therefrom that inserts into the aforesaid nozzle. Thus assembled, the filter lies between the air orifice and the aspiration tube, preventing any flow of aspirated fluids into the air orifice, and also preventing any injection of micro-organisms from the air orifice back into the aspiration line. Thus the aspiration tubing is isolated from the interior of the machine with the exception of air flow. The filter is a small hydrophobic filter of a type which will be described in detail below. The permanent machined fitting can be removed from the machine periodically and sterilized. It is significantly more durable than the disposable type used on the Cavitron/Kelman set-up kit; it provides a tight seal around the air orifice and thus improves the pressure control of the machine; and it provides a far easier technique to connect and assemble the set-up kit because it is a simple matter of inserting the male portion of the filter housing into the female portion of the fitting.

In a modified, preferred approach, the nozzle portion is hexagonally shaped and includes a threaded projection which screws into the body portion of the machined fitting. A removable locking member fits over the hexagonal nozzle to prevent rotation or loosening of the nozzle portion which may result as disposable tubing kits are emplaced and removed.

In the earlier embodiment, the nozzle occasionally became partially unscrewed as nurses or other personnel assembled the disposable portions of the set-up kit to the nozzle. It was determined that some means for preventing rotation of the nozzle was necessary and the inventor conceived and developed the removable locking tab or bracket which snaps into place over the hexagonal nozzle. The locking tab/bracket prevents any rotation or loosening of the nozzle until desired.

It is one object of the present invention to form an aspiration tube connection for machines of the type described in which the connection is made easier and simpler.

It is another object of the present invention to form an aspiration tube connection for machines of the type described in which the nozzle connection is made more secure against displacement.

Other modifications and objectives of the device will become apparent to those skilled in the art as the following detailed description of a preferred embodiment is studied in conjunction with the accompanying drawings in which:

FIG. 4 is an exploded perspective of the improved hexagonal nozzle portion and locking member; and FIG. 5 is a rear perspective view of the locking member of FIG. 4.

DETAILED DESCRIPTION OF A PREFERRED EMBODIMENT

Figure 1:
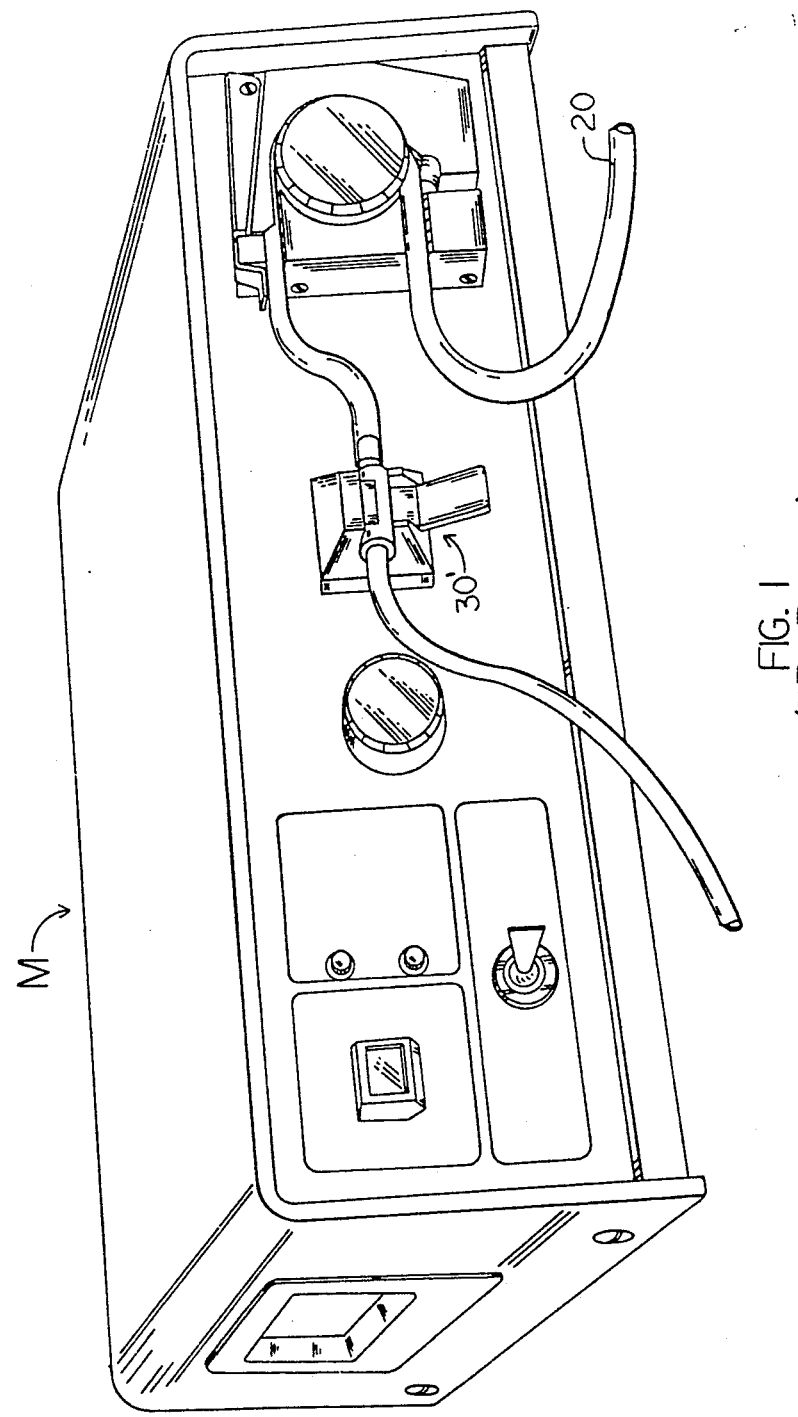
FIG. 1 is an environmental perspective view of the prior art "cam lock tee" as attached to the irrigation/aspiration machine.
Figure 2:
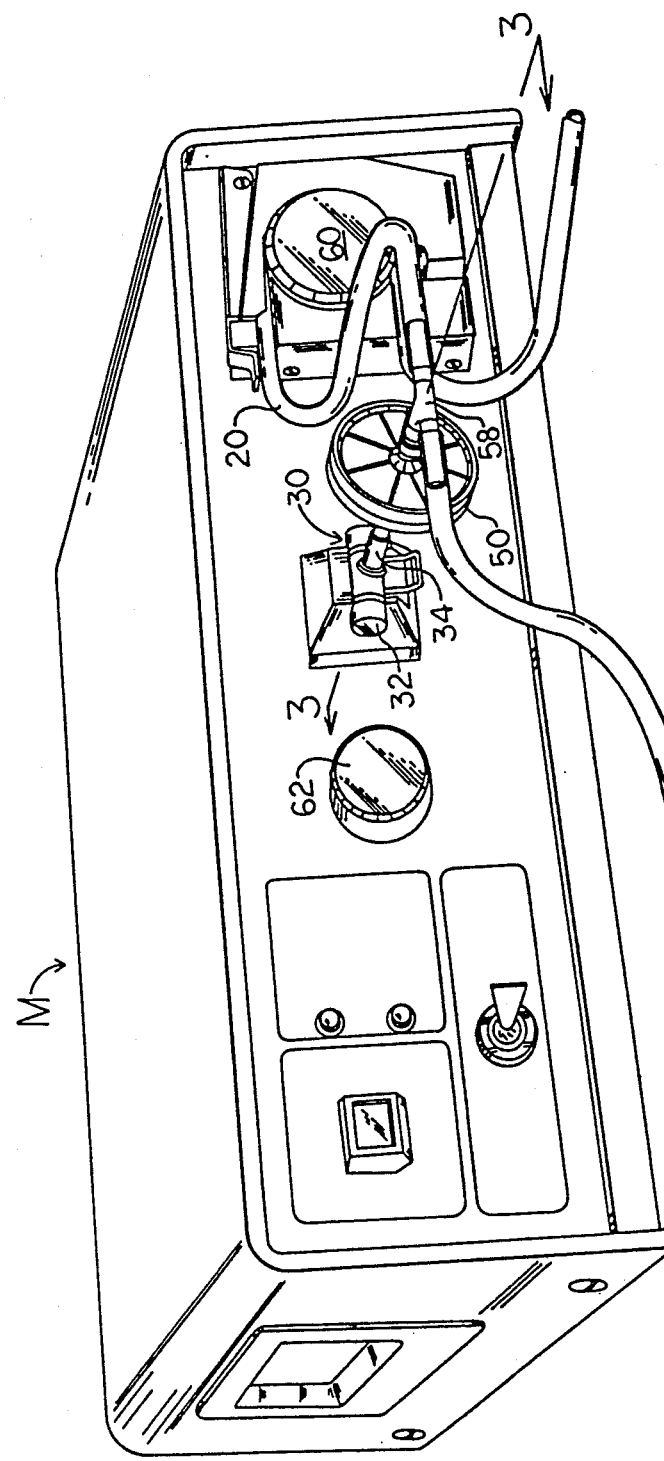
FIG. 2 is a perspective view of an irrigation/aspiration machine having the set-up kit and the machined fitting of the present invention attached thereto.

Looking first at FIG. 1 there is illustrated the irrigation/aspiration machine M having the prior art set-up kit connected thereto. The set-up kit is comprised of irrigation tubing (not shown), aspiration tubing 20, and the prior art "cam lock tee" 30'. Although it is not shown, the irrigation tubing is connected to a source of sterile fluids which supplies irrigation through the tubing to the surgical instrument and the operative site. In FIG. 2, the aspiration tubing 20 carries aspirant from the surgical instrument to a collection means. The aspiration tubing 20 is connected to the fitting receptacle 64 of the machine M by means of machined fitting 30 and coupling 58. Fitting receptacle 64 includes a passageway 42 therethrough which registers with the air outlet 40 of machine M. While coupling 58 can fit directly into fitting 30, in the preferred embodiment there is interposed a small hydrophobic filter mechanism 50. As explained above the filter device blocks the flow of aspirated liquid into the machine M through the air outlet 40, and also prevents flow of liquid containing micro-organisms and bacterial from the outlet 40 into the aspiration line. The working mechanism of the irrigation/aspiration machine M is not explained herein because it is of a conventional, known type of construction and apart from the complementing set-up kit, does not form a part of the present invention. It will suffice to explain that the aspiration line 20 is threaded through a peristaltic pumping apparatus 60 of the machine, while the irrigation tube is operatively connected to an irrigation solenoid 62 on the machine. The irrigation line is shown broken away at either end, as is the aspiration tubing 20. The saline solution or other irrigation fluid, the surgical instrument, and the collection device are not shown.

Figure 3:
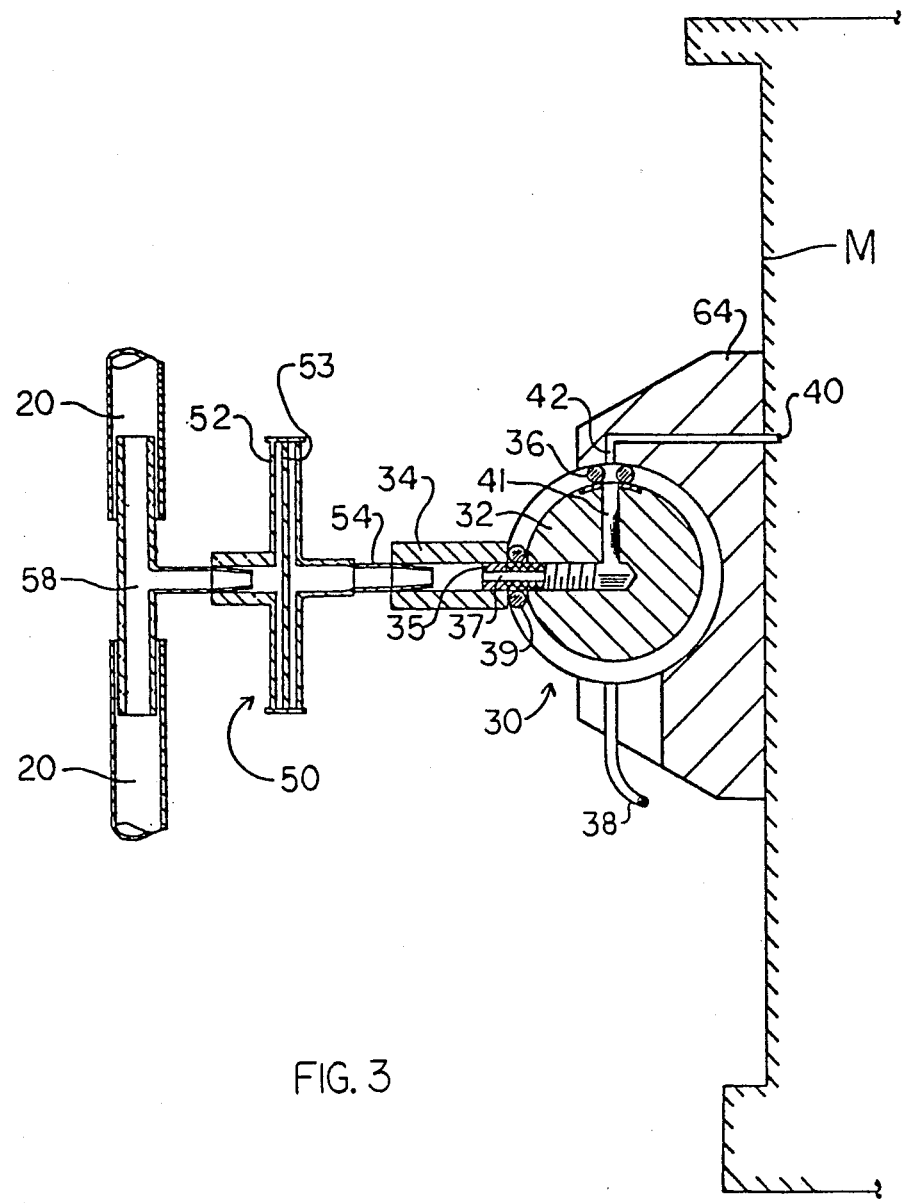
FIG. 3 is a sectional view taken substantially along lines 3—3 in FIG. 2 and illustrating the aspiration tubing rotated 90° from its actual orientation for purposes of illustration.

Looking at FIG. 1, the prior art device is shown with the accompanying "cam lock tee" 30' formed as part of the apsiration tubing. It is formed of plastic and is snapped into the same type of receptacle 64. FIG. 2 shows the present invention in its preferred embodiment with its machined fitting 30 comprised of a generally T-shaped member having a body portion 32 (shown in cross-section in FIG. 3), and an outwardly extending nozzle portion 34 providing a female jack for the male tube extending from the filter 50. Both portions 32 and 34 include air passageway therethrough as illustrated in FIG. 3 for directing air from the receptacle passageway 40 into the aspiration tube 20. As best shown in FIG. 3, the filter mechanism 50 substantially eliminates the problem of micro-organism growth in the machine portions by not allowing aspirant liquids into the machine. Also filter 50 will block passage of contaminants in the opposite direction back toward tube 20.

The fitting 30 is preferably formed of stainless steel for durability and ease in sterilization, and is merely snapped onto the receptacle 64. A passageway 41 extends through fitting 30 in operative alignment with passageway 42 for directing air from outlet 40 to the tube 20. A gasket 36 with an O-ring attached thereto surrounds the outlet from passageway 41 on the fitting body portion 32 for creating a tight seal around the outlet of passageway 42 in receptacle 64. A handle 38 simply aids in snapping the fitting 30 into the receptacle 64. It should be pointed out that the times are few when fitting 30 will be removed from receptacle 64 in the present invention. That is one of the advantages which facilitates maintaining a reliable air flow pattern. The outwardly extending portion 34 of the fitting is a hollow cylindrical shape having inner threads 35 in one end thereof. The threads 35 are screwed onto a male, outwardly threaded nipple 37 extending outwardly from member 32. When the nozzle member 34 is thus screwed onto member 32, a gasket 39 seals the joint therebetween.

FIG. 4 illustrates the improved nozzle and bracket fitting. The fitting 30 and receptacle 64 are as previously disclosed. Nozzle 34, however, has been replaced with the improved hexagonal nozzle 134 having threaded projection 136 which is received in the threaded opening in fitting 30 as shown. Other than the exterior hexagonal shape, nozzle 134 is designed and functions the same as the previously described nozzle. After the hexagonal nozzle 134 is screwed tightly into place, the snap-lock bracket or fitting 150 is snapped on over the nozzle.

The bracket 150 includes a face portion 155 from which a pair of opposing side legs or prongs 152, an upper tab 157 and a lwer tab 154 extend rearwardly. Face portion 155 further includes a hexagonal opening 156 corresponding in size and shape to the exterior shape of the nozzle 134. Small projections or nibs form gripping means 158 on the inside surface of each prong 152 grip the ends of the body 32 and serve to lock the bracket 150 into place. The legs or prongs 152 have sufficient resiliency flexibility to permit their expansion outwardly to snap the nibs 158 onto the body. Further, when assembled, the forward edge of upper tab 157 and lower tab 154 abut the adjacent facing portions of receptacle 64 to aid in positioning the bracket 150. Once positioned, bracket 150 is retained securely; and due to the hexagonal opening 156 which surrounds hexagonal nozzle 134 and due to the bracket 150, the nozzle cannot be unscrewed or loosened. The disposable tubings and filters are then connected to the nozzle as previously disclosed.

Filter device 50 is preferably a preassembled, disposable filter of a hydrophobic nature made from acrylic copolymer with a silicon repellant coating. Such filter media do not absorb liquid, rather they repel liquid. One such filter also suitable for preventing the passage of micro-organisms is sold by Gelman Sciences under the trademark ACRODISC (Models 4192 or 4184 which have pore sizes of 0.2 to 0.45 microns). As shown in cross section in FIG. 3, the filtering device 50 includes a housing 52 most often formed of a polypropylene material for maximum resistance to solvents and other chemicals; and the hydrophobic filter material or filter medium 53 retained therein. As previously explained, the filter medium is formed of an acrylic copolymer with a silicon, repellant coating. Other filters would be acceptable but must not interfere with the ability to decrease pressure at a critical point in the surgery from 370 mmHG to 0 in 300 milliseconds. The housing 52 includes a male projection 54 which slips into the portion 34 of fitting 30 and is retained therein by friction fit. The opposite end of the filter housing includes a female luer lock inlet 56 which receives a male projection from coupling 58 connected to the aspiration tubing 20.

The set-up kit described above is connected to the machine M in a conventional manner taught by the prior art. The construction outlined above in the preferred embodiment results in an improved set-up speed in that connection is effected merely by inserting the male projection 54 from the filter housing into the locked hexagonal nozzle 134 to complete connection to the air inlet. The irrigation tubing and the aspiration tubing are otherwise connected to the machine in the manner taught by the manufacturers. The same is true for connection of the tubing to the irrigating fluid bag and to the aspiration collector. Other and further modifications may be made to the embodiment described above while remaining within the scope of the claims below.

What is claimed is:

1. An aspiration apparatus for use with and releasably connected to an irrigation/aspiration machine of the type in which a suction pump continuously draws fluids into a surgical instrument away from a surgical site and along an aspirant path, said machine including a fitting receptacle on the front wall of the machine containing an air passageway into the pressure control portion of said machine through which air from the aspirant path is withdrawn to monitor suction pressure and further through which air may be selectively injected back into the aspirant path to decrease suction pressure therein; said aspiration apparatus including:
    (a) an aspiration tube selectively attachable at one end to said surgical instrument and at the other end to said pump for establishing said aspirant path which delivers aspirated fluids from the surgical site to a collection receptacle;
    (b) a T-shaped coupling means comprising a pair of opposed tubular arms colinear with and connected in line with said aspiration tube and a tubular leg depending perpendicularly therefrom, said T-shaped coupling means being positioned in an interruption in said aspiration tube upstream of said suction pump for establishing and connecting a branch path from an intermediate portion of said aspiration tube to said fitting receptacle;
    (c) said coupling means further including a fitting received in said fitting receptacle and means for releasably connecting said aspiration tube to said fitting; said fitting including a conduit therein providing communication between a first outlet registrable with said air passageway and a second outlet in communication with releasable connecting means for the passage of air therethrough; and a nozzle member detachably connected to said fitting; said nozzle having a hexagonal exterior shape and further including a non-rotatable snaplock bracket removably attached thereto to prevent loosening of said nozzle from said body portion;
    (d) the depending leg of said T-shaped coupling means including a filter means interposed therein between said fitting receptacle on said irrigation/aspriation machine and said aspiration tube for preventing flow of aspirated liquid and microorganisms from said aspiration tube into the pressure control portion of said irrigation/aspiration machine and for preventing any residual microorganic growth and liquid being transmitted from within the pressure control portion of said irrigation/aspiration machine into said aspirant path;
    (e) said filter means comprising a housing having means for passage of air in either direction therethrough; a hydrophobic filter medium disposed within said housing in the fluid passageway; said hydrophobic filter medium having the characteristics of passing air and blocking the passage of liquids in both directions and having a pore size sufficiently small as to block the flow of contaminating or infectious microorganisms in both directions.

2. An aspiration apparatus to claim 1 wherein said snap-lock bracket comprises a face plate having an aperture therein and a pair of opposing, parallel prongs depending therefrom; said aperture having an hexagonal shape corresponding in size and shape to the exterior shape of said nozzle; and said prongs having sufficient flexibility to engage and grip the sides of said fitting when said aperture is positioned around said hexagonal nozzle; whereby said bracket is inserted around said nozzle and said such that said prongs engage and grip said fitting and said aperture surrounds said hexagonal nozzle to prevent movement thereof.

3. An aspiration apparatus for use with and releasably connected to an irrigation/aspiration machine of a type in which a suction pump continuously draws fluids into a surgical instrument and away from a surgical site along an aspirant path, said machine including a fitting receptacle having a generally cylindrical seat therein attached to the front wall of said irrigation/aspiration machine and containing a first air passageway into the pressure control portion of said machine through which air from the aspirant path is withdrawn to monitor the suction pressure and further through which air may be selectively injected into the aspirant path to decrease suction pressure therein; said aspiration apparatus comprising:
    (a) an aspiration tube selectively attachable at one end to said surgical instrument and at the other end to said pump for establishing said aspirant path which delivers aspirated fluids from the surgical site to a collecting receptacle;
    (b) a fitting including a generally cylindrical body portion substantially permanently retained in said fitting receptacle seat;
    (c) a coupling means positioned in an interruption in said aspiration tube upstream of said suction pump for establishing and operatively connecting said aspiration tube to said fitting receptacle, said coupling means comprising a substantially permanent fitting seated in said fitting receptacle and a branch tube having a pair of opposed tubular arms colinear with and connected in line with said aspiration tube and a tubular leg extending perpendicular to and in communication with said aspiration tube, said branch tube selectively engageable with said fitting for releasably connecting said aspiration tube to said fitting, further wherein said coupling means comprises a nozzle member detachably connected to said body portion; said nozzle having an hexagonal exterior shape and further including a non-rotatable snap-lock bracket removably attached thereto to prevent loosening of said nozzle from said body portion;

(d) said fitting, when properly seated, having a second air passageway extending transversely therethrough in registry with both said first air passageway and the interior of said branch tube for establishing an air path through said fitting and said branch tube for the passage of air in both directions between said aspiration tube and the inside of said irrigation/aspiration machine;

(e) said branch tube being separable from said fitting whereby said cylindrical body portion remains positioned in said substantially permanent fitting receptacle seat as a plurality of said aspiration tubes and branch tubes are emplaced and removed for a plurality of successive surgical operations therewith.

4. An aspiration assembly according to claim 3 wherein said snap-lock bracket comprises a face plate having an aperture therein and a pair of opposing, parallel prongs depending therefrom; said aperture having an hexagonal shape corresponding in size and shape to the exterior shape of said nozzle; and said prongs having sufficient flexibility to engage and grip the sides of said body portion when said aperture is positioned around said hexagonal nozzle; whereby said bracket is inserted around said nozzle and body portion such that said prongs engage and grip said body portion and said aperture surrounds said hexagonal nozzle to prevent movement thereof.

5. In an irrigation/aspiration machine which includes a suction pump, an aspiration tube for removing aspirants from an operative site to a collecting receptacle, and a receptacle on said machine having a permanent fitting received therein for connecting said aspiration tube to said machine, and wherein said receptacle and said fitting contain an air passageway therethrough so that the air pressure within said aspiration tube may be sampled and air may be injected by said machine into said tube to decrease suction pressure therein, the improvement comprising a coupling means associated with said aspiration tube for releasably connecting said tube to said permanent fitting; said coupling means and said tube being disposable after each operation and said fitting remaining attached in position in said receptacle as a permanent part of said machine, wherein said coupling means comprises a nozzle member detachably connected to said fitting; said nozzle having an hexagonal exterior shape and further including a non-rotatable snap-lock bracket removably attached thereto to prevent loosening of said nozzle from said fitting.

* * * * *